(12) United States Patent
Dutta et al.

(10) Patent No.: US 8,057,653 B2
(45) Date of Patent: Nov. 15, 2011

(54) CARBON DIOXIDE SENSOR

(75) Inventors: Prabir K. Dutta, Worthington, OH (US); Inhee Lee, Columbus, OH (US); Sheikh A. Akbar, Hilliard, OH (US)

(73) Assignee: Ohio State Research Foundation, Columbus, OH (US)

( * ) Notice: Subject to any disclaimer, the term of this patent is extended or adjusted under 35 U.S.C. 154(b) by 124 days.

(21) Appl. No.: 11/974,580

(22) Filed: Oct. 15, 2007

(65) Prior Publication Data
US 2009/0095626 A1    Apr. 16, 2009

(51) Int. Cl.
*G01N 27/407* (2006.01)
(52) U.S. Cl. ............................... 204/424; 205/784
(58) Field of Classification Search .............. 204/424, 204/431; 205/784, 784.5
See application file for complete search history.

(56) References Cited

U.S. PATENT DOCUMENTS

| | | | |
|---|---|---|---|
| 5,194,134 A * | 3/1993 | Futata et al. ............... | 204/421 |
| 6,190,519 B1 * | 2/2001 | Kobayashi et al. ......... | 204/426 |
| 6,325,905 B1 * | 12/2001 | Matsui et al. .............. | 204/424 |
| 7,006,926 B2 * | 2/2006 | Ono et al. .................. | 702/24 |

OTHER PUBLICATIONS

Figueroa et al, Sensors and Actuators B, 107 (2005), pp. 839-848.*

* cited by examiner

*Primary Examiner* — Kaj K Olsen
(74) *Attorney, Agent, or Firm* — Daniel J. Schlue; Roetzel & Andress (57) ABSTRACT

The present invention generally relates to carbon dioxide ($CO_2$) sensors. In one embodiment, the present invention relates to a carbon dioxide ($CO_2$) sensor that incorporates lithium phosphate ($Li_3PO_4$) as an electrolyte and sensing electrode comprising a combination of lithium carbonate ($Li_2CO_3$) and barium carbonate ($BaCO_3$). In another embodiment, the present invention relates to a carbon dioxide ($CO_2$) sensor has a reduced sensitivity to humidity due to a sensing electrode with a layered structure of lithium carbonate and barium carbonate. In still another embodiment, the present invention relates to a method of producing carbon dioxide ($CO_2$) sensors having lithium phosphate ($Li_3PO_4$) as an electrolyte and sensing electrode comprising a combination of lithium carbonate ($Li_2CO_3$) and barium carbonate ($BaCO_3$).

39 Claims, 9 Drawing Sheets

Figure 1

Response transient of the sensor with $BaCO_3$ coated on $Li_2CO_3$ in dry and humid $CO_2$ at 500°C

Figure 2

Response transient of the sensor with (a) pure $Li_2CO_3$ and (b) physical mixture of $BaCO_3$-$Li_2CO_3$ in dry and humid $CO_2$ at 500°C

Figure 3

The dependence of EMF on log [$CO_2$ concentration] for the sensors with pure $Li_2CO_3$ (— —) and $BaCO_3$ coated on $Li_2CO_3$ (····) in dry and humid conditions at 500°C

Figure 4

The long-term test of the sensor with BaCO$_3$ coated on Li$_2$CO$_3$ (a) for 9 hrs continuous test and (b) for 60 days test in humid condition at 500°C

XRD diffraction pattern for (a) pure BaCO₃ (b) BaCO₃ coated on Li₂CO₃ and (c) pure Li₂CO₃

Figure 7

(a) SEM image of the surface of BaCO$_3$ coated on Li$_2$CO$_3$ powder and (b) mapping of Ba content by EDS

Figure 8

The cross-sectional images of $BaCO_3$ coated on $Li_2CO_3$ by (a) FIB and (b) TEM

Figure 9

CARBON DIOXIDE SENSOR

This work was supported by CISM through the Department of Energy Contract No. DE-FC26-03NT41615 and, as such, the United States government may have certain rights thereto.

FIELD OF THE INVENTION

The present invention generally relates to carbon dioxide ($CO_2$) sensors. In one embodiment, the present invention relates to a carbon dioxide ($CO_2$) sensor that incorporates lithium phosphate ($Li_3PO_4$) as an electrolyte and sensing electrode comprising a combination of lithium carbonate ($Li_2CO_3$) and barium carbonate ($BaCO_3$). In another embodiment, the present invention relates to a carbon dioxide ($CO_2$) sensor has a reduced sensitivity to humidity due to a sensing electrode with a layered structure of lithium carbonate and barium carbonate. In still another embodiment, the present invention relates to a method of producing carbon dioxide ($CO_2$) sensors having lithium phosphate ($Li_3PO_4$) as an electrolyte and sensing electrode comprising a combination of lithium carbonate ($Li_2CO_3$) and barium carbonate ($BaCO_3$).

BACKGROUND OF THE INVENTION

Carbon dioxide sensors are becoming increasingly important for monitoring air-quality, measuring metabolic activity of animals and controlling combustion. While there are commercial sensors for air quality monitoring, no reliable sensor exits for high-temperature combustion-related applications. Among several designs for cost effective carbon dioxide ($CO_2$) sensor with high sensitivity and selectivity, the potentiometric type sensor that consists of $Na^+$ or $Li^+$ conductor, a metal carbonate sensing electrode and a reference electrode were thought to be promising because they exhibit satisfactory EMF signals over a wide range gas concentrations and temperatures (see, e.g., Y. Saito and T. Maruyama; *Recent Developments of Sensors for Carbon Oxides Using Solid Electrolytes*; Mid State Ionics 28 to 30; (1988); pp. 1644 to 1647 and C. Park, C. Lee, S. Akbar, and J. Hwang; *The Origin of Oxygen Dependence in a Potentiometric $CO_2$ Sensor with Li-Ion Conducting Electrolytes*; Sensors and Actuators B; 88; (2003); pp. 53 to 59). However, such sensors suffer from various drawbacks including but not limited to, limited effectiveness in humid conditions.

Potentiometric sensors based on a $Na^+$ conductor such as NASICON® (see, e.g., Y. Saito and T. Maruyama; *Recent Developments of Sensors for Carbon Oxides Using Solid Electrolytes*; Mid State Ionics 28 to 30; (1988); pp. 1644 to 1647) attached to a $Na_2CO_3$ sensing electrode are reported to respond well to changes in $CO_2$ concentration, following Nernst's equations when dry $CO_2$ is used. The time required for 90% response is, however, reported to be several minutes at 500 to 700° C. A major problem with these sensors is that they suffer from strong interference from humidity.

Attempts to improve the sensor performance by modification of the sensing electrode material are described for the first time in references (see, e.g., N. Miura, S. Yao, Y. Shimizu, N. Yamazoe; *High Performance Solid Electrolyte Carbon Dioxide Sensor with a Binary Carbonate Electrode*; Sensors and Actuators B; 9; (1992); pp. 165 to 170; and S. Yao, Y. Shimizu, N. Miura, N. Yamazoe; *Solid Electrolyte Carbon Dioxide Sensor Using Sodium-Ion Conductor and $Li_2CO_3$—$BaCO_3$ Electrode;* Japanese Journal of Applied Physics, Part 2,31; (1992); pp. 197 to 199). The sensor using binary carbonate ($Na_2CO_3$—$BaCO_3$) reportedly exhibits a faster response than a sensor that employs $Na_2CO_3$ alone when $BaCO_3$ content is more than a critical amount (see, e.g., S. Yao, Y. Shimizu, N. Miura, N. Yamazoe; *Solid Electrolyte Carbon Dioxide Sensor Using Sodium-Ion Conductor and $Li_2CO_3$—$BaCO_3$ Electrode;* Japanese Journal of Applied Physics, Part 2,31; (1992); pp. 197 to 199).

Thus, there is a need in the art for improved $CO_2$ sensors that work across a wide range of temperatures, as well as $CO_2$ sensors that are less sensitive to humidity.

SUMMARY OF THE INVENTION

The present invention generally relates to carbon dioxide ($CO_2$) sensors. In one embodiment, the present invention relates to a carbon dioxide ($CO_2$) sensor that incorporates lithium phosphate ($Li_3PO_4$) as an electrolyte and sensing electrode comprising a combination of lithium carbonate ($Li_2CO_3$) and barium carbonate ($BaCO_3$). In another embodiment, the present invention relates to a carbon dioxide ($CO_2$) sensor has a reduced sensitivity to humidity due to a sensing electrode with a layered structure of lithium carbonate and barium carbonate. In still another embodiment, the present invention relates to a method of producing carbon dioxide ($CO_2$) sensors having lithium phosphate ($Li_3PO_4$) as an electrolyte and sensing electrode comprising a combination of lithium carbonate ($Li_2CO_3$) and barium carbonate ($BaCO_3$).

In one embodiment, the present invention relates to a carbon dioxide sensor comprising: an alkaline metal phosphate substrate; at least two conductive leads; at least one reference electrode; and at least one sensing electrode, wherein the sensing electrode is formed from an alkaline carbonate coated with an alkaline earth carbonate.

In another embodiment, the present invention relates to a carbon dioxide sensor comprising: a lithium phosphate substrate; at least two conductive leads; at least one reference electrode; and at least one sensing electrode, wherein the sensing electrode is formed from lithium carbonate coated with barium carbonate and wherein the sensor exhibits sensitivity up to a temperature of at least about 700° C.

In still another embodiment, the present invention relates to a carbon dioxide sensor comprising: a lithium phosphate substrate; at least two conductive gold leads; at least one reference electrode formed from a combination of lithium titanate and titanium (IV) oxide; and at least one sensing electrode formed from lithium carbonate coated with barium carbonate, wherein the sensor exhibits sensitivity up to a temperature of at least about 700° C. regardless of the level of relative humidity present.

BRIEF DESCRIPTION OF THE DRAWINGS

FIGS. 8(*a*) and 8(*b*) are (a) an SEM image of the surface of $BaCO_3$ coated on $Li_2CO_3$ powder and (b) mapping of Ba content by EDS; and FIGS. 9(*a*) and 9(*b*) are cross-sectional images of $BaCO_3$ coated on $Li_2CO_3$ by (a) FIB and (b) TEM.

DETAILED DESCRIPTION OF THE INVENTION

The present invention generally relates to carbon dioxide ($CO_2$) sensors. In one embodiment, the present invention relates to a carbon dioxide ($CO_2$) sensor that incorporates lithium phosphate ($Li_3PO_4$) as an electrolyte and sensing electrode comprising a combination of lithium carbonate ($Li_2CO_3$) and barium carbonate ($BaCO_3$). In another embodiment, the present invention relates to a carbon dioxide ($CO_2$) sensor has a reduced sensitivity to humidity due to a sensing electrode with a layered structure of lithium carbonate and barium carbonate. In still another embodiment, the present invention relates to a method of producing carbon dioxide ($CO_2$) sensors having lithium phosphate ($Li_3PO_4$) as an electrolyte and sensing electrode comprising a combination of lithium carbonate ($Li_2CO_3$) and barium carbonate ($BaCO_3$).

In one embodiment, the present invention relates to carbon dioxide ($CO_2$) sensors built with a sensing electrode comprising a mixture of an alkali carbonate and an alkaline earth carbonate, where such a sensing electrode exhibits better stability against humidity than those based on single carbonate. While not wishing to be bound to any one theory, one possible reason for such improved behavior is due to the better stability of the binary carbonate against water vapor. In one embodiment, such an alkali carbonate and an alkaline earth carbonate binary carbonate system is composed of a $Li_2CO_3$—$BaCO_3$ binary system. In another embodiment, the sensing electrode of the present invention is a layer, or some other three dimensional shape, of $Li_2CO_3$ coated with $BaCO_3$.

In one embodiment, carbon dioxide sensors in accordance with the present invention can operate at a wide range of temperatures including high temperatures of up to about 400° C., up to about 500° C., up to about 600° C., or even up to about 700° C. In another embodiment, carbon dioxide sensors in accordance with the present invention are less sensitive, or even immune, to influence by humidity and can operate at any relative humidity level including, but not limited to, up to about 50 percent relative humidity, up to about 60 percent relative humidity, up to about 70 percent relative humidity, up to about 80 percent relative humidity, up to about 90 percent relative humidity, up to about 95 percent relative humidity, up to about 97 percent relative humidity, up to about 99 percent relative humidity, or even at 100 percent relative humidity. It should be noted that the either set of individual range limits above can be combined to form various closed end ranges.

Figure 1:
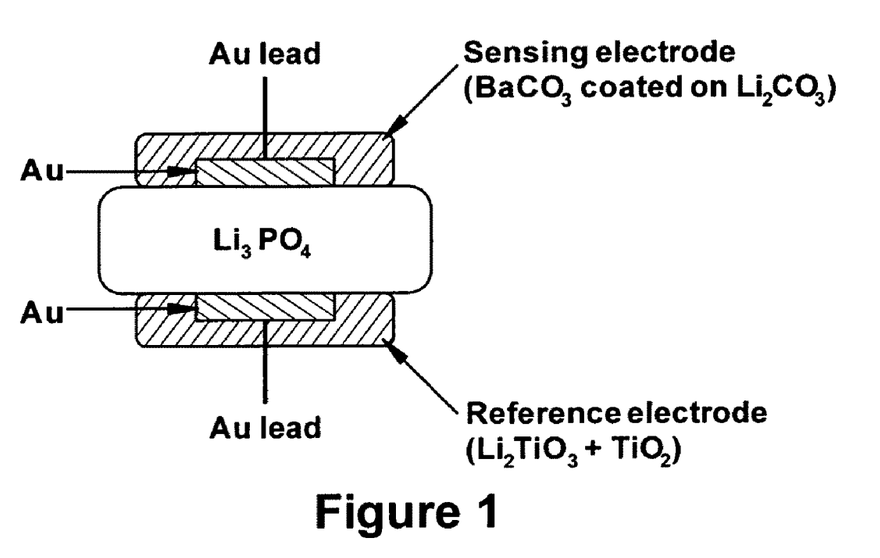
FIG. 1 is a schematic illustration of a carbon dioxide sensor in accordance with one embodiment of the present invention.

Fabrication of Sensor Elements:

Turning to FIG. 1, FIG. 1 illustrates a carbon dioxide sensor according to one embodiment of the present invention. In the sensor of FIG. 1 the carbon dioxide sensor is formed from lithium phosphate ($Li_3PO_4$, available from Alfa Aesar, 99.5%) added with 5 mole percent of $SiO_2$ to enhance the sinterability used as an electrolyte. The powder mixture is ball-milled in ethanol for about 8 hours and dried at about 120° C. The dried mixture is compacted into a disc at 1.5 kpsi and sintered at 800° C. for about 8 hours with a heating and cooling rate of 3° C./min. A Lindbergh furnace (Model 51732-B) is utilized for the heat treatment. On both sides of the $Li_3PO_4$ electrolyte disk of 1.2 in diameter and 0.8 mm thick, gold paste (Heraeus Gold ink) is painted with a diameter of 4 mm. It is cured at 700° C. for 1 about an hour at a heating/cooling rate of 3° C./mh in a Lindberg box furnace.

Lithium titanate ($Li_2TiO_3$, Lithium Corporation of America Inc., 99%) mixed with 5 m/o of titania ($TiO_2$, Alpha Aesar, 99.9%) is used as the reference electrode. The powder mixture is ball-milled in ethanol. It is then mixed with an α-terpineol organic binder (available from Fisher Chemicals) and painted on the surface of the $Li_3PO_4$ electrolyte. It is cured following the same heat treatment profile of the gold paste cuing. In order to compare the sensing behaviors, the sensing electrode is fabricated with three different materials: (A) pure lithium carbonate; (B) a physical mixture of lithium carbonate and barium carbonate with a molar ratio of 1:1; and (C) lithium carbonate with a coating layer of barium carbonate. For the sensor with electrode A, lithium carbonate ($Li_2CO_3$, Alpha Aesar, 99%) is ball-milled in ethanol and painted on the surface of the $Li_3PO_4$ electrolyte by hand-painting and cured at 600° C. for bout one hour at a heating and cooing rate of 3° C./min. For the sensor with electrode B, lithium carbonate and barium carbonate ($BaCO_3$, available from J.T. Baker Chemical Company, 99%) is mixed in a 1:1 molar ratio, ball-milled in ethanol and painted by hand-painting. In order to avoid the eutectic reaction (at 609±4° C.) of $Li_2CO_3$ and $BaCO_3$, the sensor is cured at 500° C. for about 3 hours at a heating and cooing rate of 3° C./min. For the sensor with electrode C, the coating layer of $BaCO_3$, the powder of $BaCO_3$ coated on $Li_2CO_3$ is painted and cured under the same condition as that of electrode B. The following process is used to coat $Li_2CO_3$ with $BaCO_3$.

In the coating process, barium nitrate ($Ba(NO_3)_2$, available from Johnson Matthey, 99.999%) is used as a $BaCO_3$ precursor. Next, an 0.2 M $Ba(NO_3)_2$ aqueous solution is prepared in de-ionized water using magnetic stirring. Two weight percent $Li_2CO_3$ powder is added into the $Ba(NO_3)_2$ solution, and then water is removed by heating in rota-evaporator. For $Ba(NO_3)_2$ decomposition and reaction with $CO_2$ gas, the dried powder is heat-treated at 580° C. for about 3 hours under $CO_2$ atmosphere. During the heat treatment, $BaCO_3$ is coated on the surface of the $Li_2CO_3$ powder.

Measurement of Sensing Properties:

For sensing tests, the sensor is located in the central uniform temperature zone of a Lindberg horizontal tube furnace. Three gases $N_2$, air, and $CO_2$ are mixed for the sensing tests. Sample gases are prepared from pure $CO_2$ diluted in nitrogen by mining it with air. The $CO_2$ gas concentration from 5% to 20% is controlled by mixing. The gases are vented out through a water bubbler into the exhaust pipe. Humid gas is prepared by allowing gas mixture to be bubbled through water at room temperature. In humidity tests, the relative humidity is 80%. The test temperature is 500° C. The EMF values of the sensor are measured by a two-probe technique with a model HP 34401A voltmeter.

Microscopy and XRD Analysis:

The micro-structural observation and phase analyses of the coated samples are done by using XRD, SEM, TEM and FIB. The surface image of the sensing electrode is observed by scanning electron microscope (SEM, Quanta, FEI), and the cross-sectional images of the sensing electrode and the thickness of $BaCO_3$ coating layer is investigated by focused ion beam (FIB, Strata DB235, FEI) and transmission electron microscope (TEM, CM 200, FEI). The phase analyses of pure $Li_2CO_3$ and $BaCO_3$ coated on $Li_2CO_3$ system are determined using Scintag PAD-V diffractometer with Cu Kα radiation at 45 kV and 20 mV in 2θ range from 10 to 70°. JCPDS standard data are compared to the spectra for phase identification.

Figure 2:
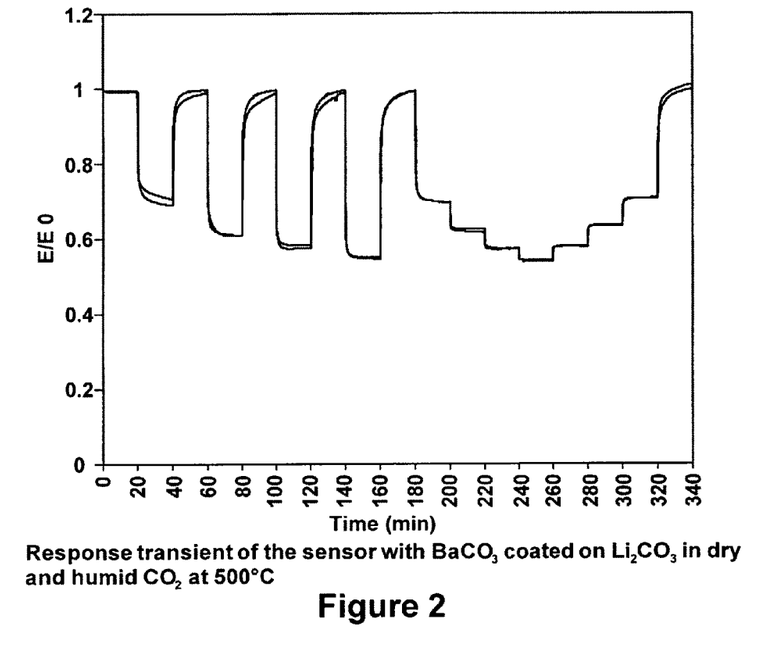
FIG. 2 is a graph illustrating the response transient of a sensor with $BaCO_3$ coated on $Li_2CO_3$ in dry and humid $CO_2$ at 500° C.

Sensing Properties:

FIG. 2 shows the response transients to dry and humid $CO_2$ gas from 0% to 20% at 500° C. for a sensor with electrode C, $BaCO_3$ coated on $Li_2CO_3$. The sensor showed a good $CO_2$ sensing behavior under both dry and humid conditions. At all $CO_2$ concentrations, the EMF values (by the base line EMF value) are very similar under both dry and humid conditions. The difference of sensitivity between dry and humid conditions is less than 2%. It is found that the response transients of the sensor are hardly affected by water vapor though the response of the sensor became slightly sluggish. The 80% response time of the sensor is 14 seconds under dry conditions, and 54 seconds under humid conditions. In addition, the sensor showed fast recovery under humid conditions.

Figure 3:
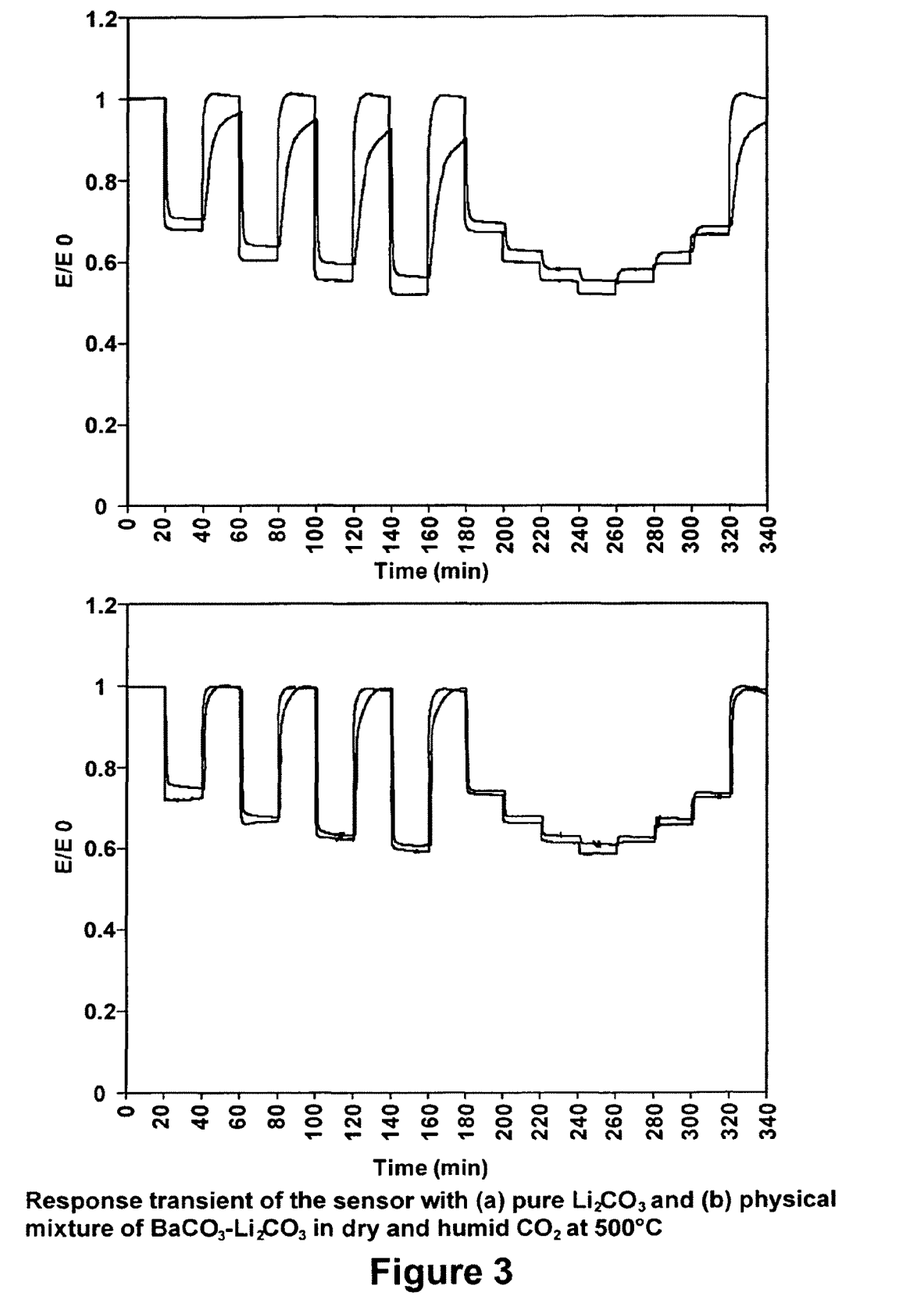
FIGS. 3(a) and 3(b) are graphs illustrating the response transient of a sensor with (a) pure $Li_2CO_3$ and (b) a physical mixture of $BaCO_3$—$Li_2CO_3$ in dry and humid $CO_2$ at 500° C.

For comparison, FIG. 3 shows the response transients of the sensors with electrode A (pure $Li_2CO_3$) and electrode B (the physical mixture of $Li_2CO_3$—$BaCO_3$) at 500° C. with dry and humid $CO_2$ gas. As seen from FIG. 3, the response transients of the sensors to dry $CO_2$ gas are quite reasonable. However, the response is seriously affected by the presence of water vapor. In FIG. 3(a), for the sensor with pure $Li_2CO_3$, the difference of sensitivity between dry and humid test became larger from 4% to 9%. Under humid conditions, the response and the recovery are very slow, although the sensor with the physical mixture of $Li_2CO_3$—$BaCO_3$ shows a better recovery and a smaller difference in sensitivity compared to the sensor with pure $Li_2CO_3$, as shown in FIG. 3(b).

Figure 4:
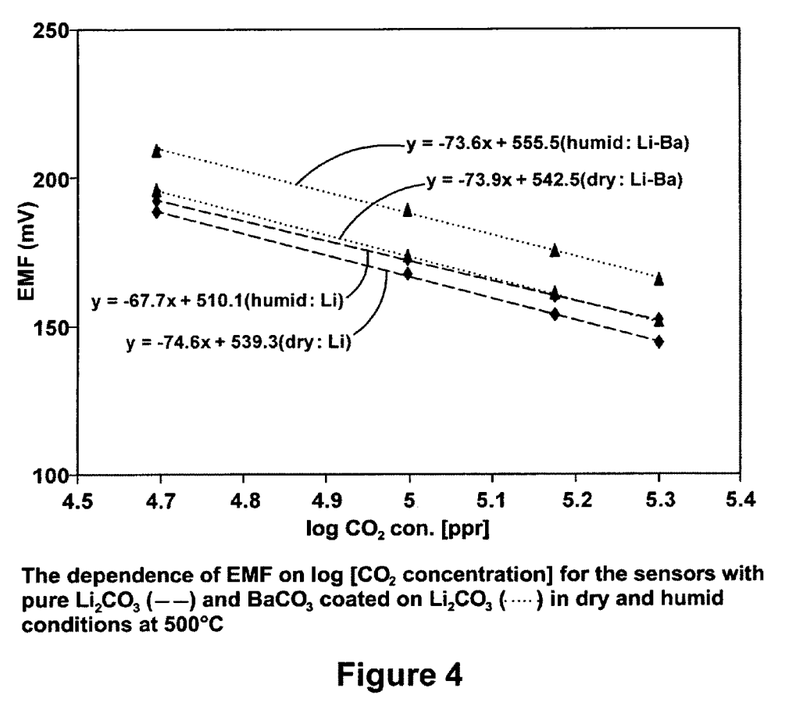
FIG. 4 is a graph illustrating the dependence of EMF on log [$CO_2$ concentration] for sensors with pure $Li_2CO_3$ and $BaCO_3$ coated on $Li_2CO_3$ in dry and humid conditions at 500° C.

FIG. 4 shows the Nerstian behavior of the sensors with electrode A (pure $Li_2CO_3$) and electrode C ($BaCO_3$ coated on $Li_2CO_3$) at 500° C. under dry and humid conditions. For the sensor with $BaCO_3$ coated on $Li_2CO_3$, the EMF values changed linearly with the logarithm of $CO_2$ concentration in the entire range tested under both dry and humid conditions with a Nerstian slope of 73.9 mV/decade and 73.6 mV/decade. These values of the Nerstian slope are very similar to the theoretical value at 500° C. 76.6 mV/decade. For the sensor with pure $Li_2CO_3$, the Nerstian slope for the dry condition is 74.6 mV/decade and for the humid condition is 67.7 mV/decade.

Figure 5:
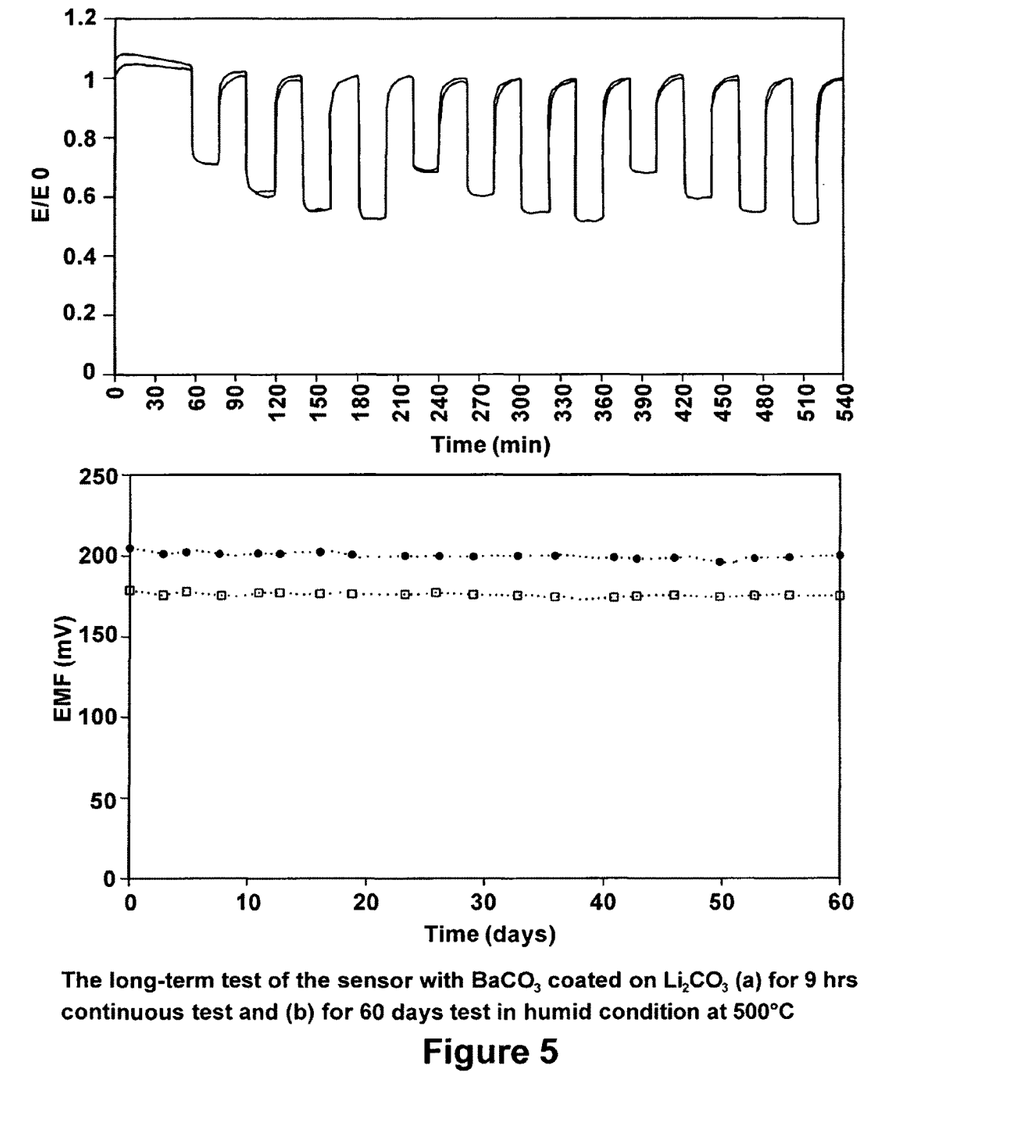
FIGS. 5(a) and 5(b) are graphs illustrating the long-term test of the sensor with $BaCO_3$ coated on $Li_2CO_3$ (a) for a 9 hour continuous test and (b) for a 60 day test in humid condition at 500° C.

In order to check long-term stability against humidity sensing behaviors are investigated at 500° C. for 9 hours continuously and for 60 days with an interval of 2 to 3 days under humid conditions. FIG. 5(a) shows the sensing behavior of the sensor with $BaCO_3$ coated on $Li_2CO_3$ for 9 hours under dry and humid conditions. During the 9 hour continuous humidity test, the EMF values show good match with those for the dry test. FIG. 5(b) shows the EMF values at 5% and 10% $CO_2$ for 60 days under humid conditions. As shown in FIG. 5(b), it can be seen that the sensor signals are sufficiently stable during the test period of about 60 days.

Figure 6:
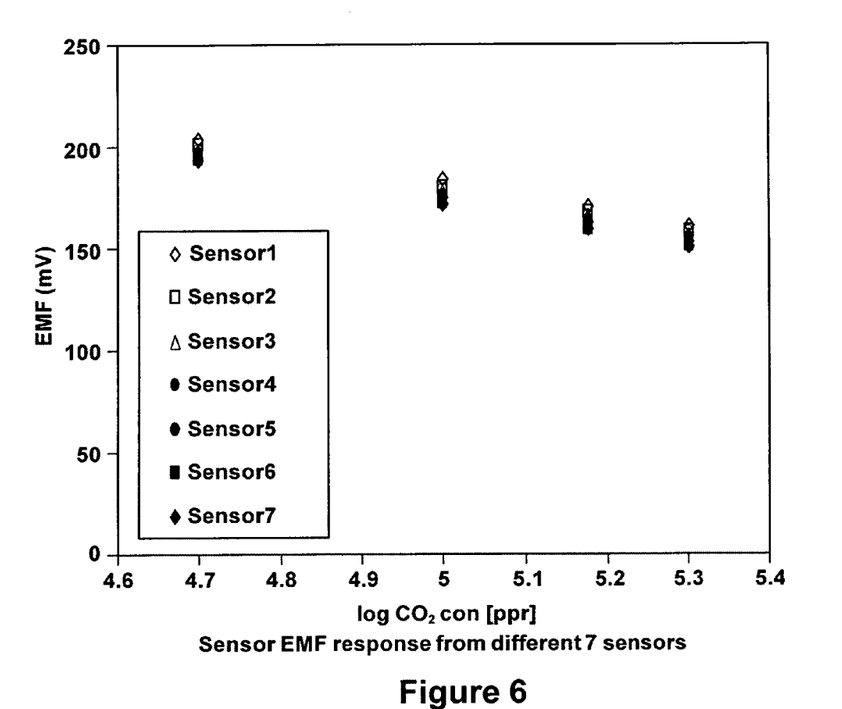
FIG. 6 is a graph illustrating sensor EMF response from seven different sensors.

When 7 sensors with $BaCO_3$ coated on $Li_2CO_3$ are fabricated using the same procedure they showed similar behavior under the humid condition. The Nerstian slope of the 7 different sensors show about 1.3 standard deviations as can be seen from FIG. 6. Under humid conditions, the maximum Nerstian slope is 73.6 and the minimum was 70.4. The sensors show very good reproducibility.

Figure 7:
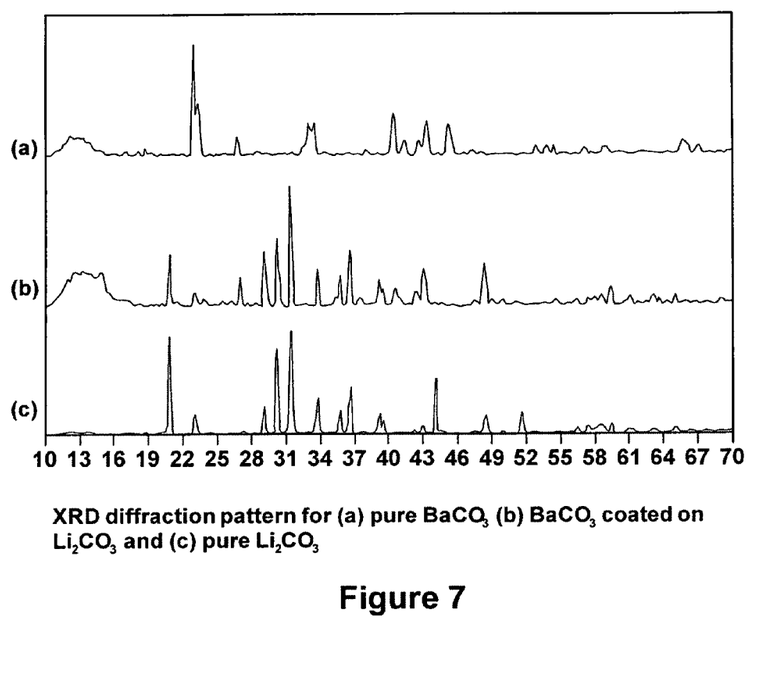
FIG. 7 is a graph illustrating XRD diffraction pattern for (a) pure $BaCO_3$; (b) $BaCO_3$ coated on $Li_2CO_3$; and (c) pure $Li_2CO_3$.

Sensing Electrode of $BaCO_3$ Coated on $Li_2CO_3$:

FIG. 7 shows X-ray diffraction patterns obtained for $BaCO_3$ coated on $Li_2CO_3$ powder. Together with this data, the XRD pattern for pure $BaCO_3$ and $Li_2CO_3$ are shown for comparison. All peaks observed for $BaCO_3$ coated on $Li_2CO_3$ powder are identified as either $BaCO_3$ or $Li_2CO_3$ phase. No shift in peak positions is observed. These results suggest that lithium and barium carbonates do not form substitutional solid solutions. Such a conclusion seems to be justified taking into account the differences in crystal structures ($Li_2CO_3$-monoclinic, $BaCO_3$-orthorhombic), ionic radii ($Li^+$0.59 Angstroms, $Ba^{2+}$1.36 Angstroms) and valences of both ions.

Figure 8:
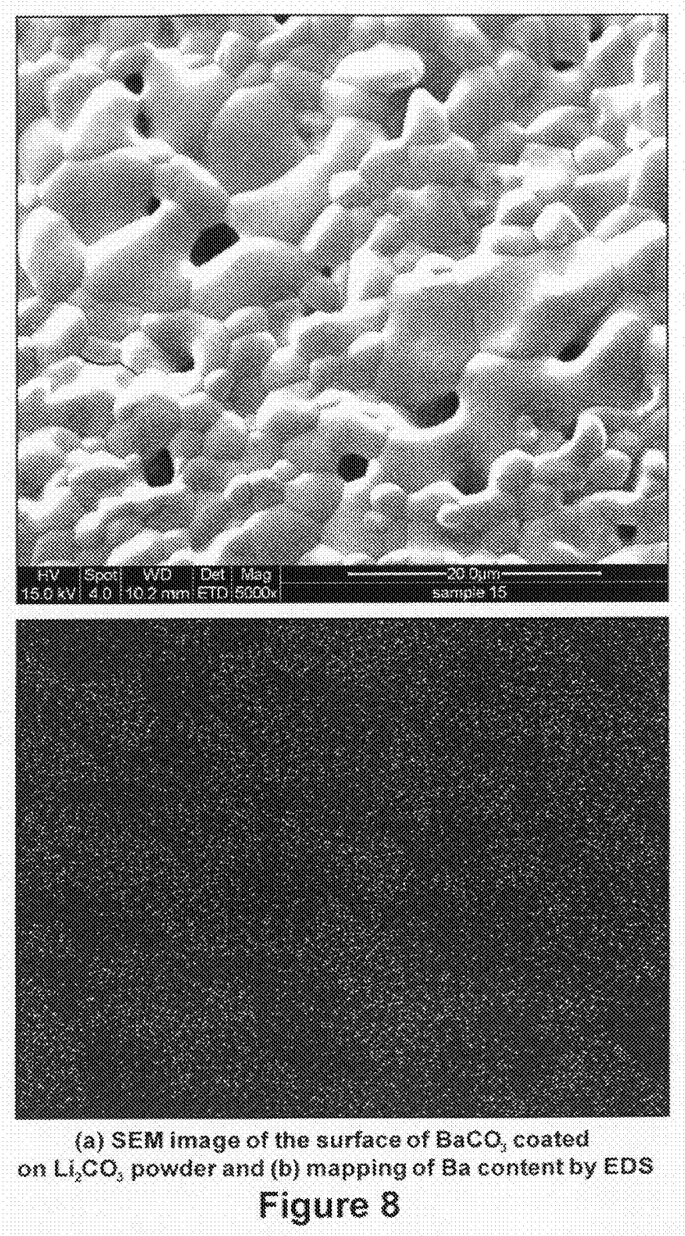

In order to investigate the chemical composition and homogeneity of the samples, an electron diffraction spectroscopy analysis technique is used in conjunction with scanning electron microscopy (SEM-EDS, Qunata). FIG. 8(a) shows $BaCO_3$ coated on $Li_2CO_3$ powder with smooth surface morphology. The distribution of the Ba element within the sensing electrode is examined using EDS element mapping on the SEM, as shown in FIG. 8(b). The data reveals a homogenous distribution of Ba on the surface. This indicates that the $Li_2CO_3$ powders have a uniform and continuous $BaCO_3$ coating layer. This uniform coating may be attributed to the fact that $Li_2CO_3$ powder remains dispersed during the coating process by rota-evaporator due continuous rotation.

Figure 9:
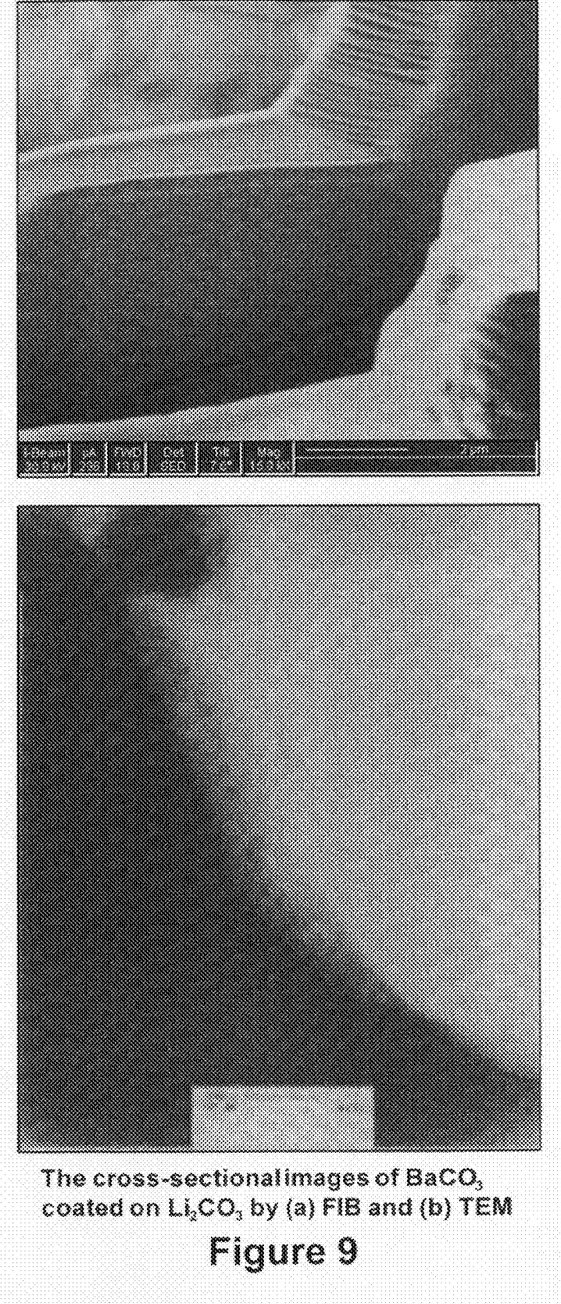

FIG. 9(a) shows the cross-sectional image of the sensing electrode by FIB. Due to different contrast of materials, two layers are observed by ion beam. The outer thin layer is $BaCO_3$ and the inner layer is $Li_2CO_3$. A representative TEM image of $BaCO_3$ coated on $Li_2CO_3$ powder is shown in FIG. 9(b). The $Li_2CO_3$ surface is covered with a continuous $BaCO_3$ coating layer. The thickness of $BaCO_3$ coating layers is around 300 nm.

$CO_2$ Sensing Mechanism:

The current sensors are composed of the following solid-state electrochemical cell: Air, $CO_2$, Au|$BaCO_3$ coated on $Li_2CO_3$|$Li_3PO_4$|$Li_2TiO_3$+$TiO_2$|Au, $CO_2$, Air. The sensing electrode composed of binary carbonate system such as $Li_2CO_3$ and $BaCO_3$ has been investigated by earlier researchers (see, e.g., S. Yao, Y. Shimizu, N. Miura, N. Yamazoe; *Solid Electrolyte Carbon Dioxide Sensor Using Sodium-Ion Conductor and $Li_2CO_3$—$BaCO_3$ Electrode*, Japanese Journal of Applied Physics; Part 2,31 (1992); pp. 197 to 199; and P. Pasierb, S. Komornicki, R. Gajerski, S. Kozinski, M. Rekas; *The Performance and Long-Time Stability of Potentiometric $CO_2$ Gas Sensors Based on the (Li—Ba)$CO_3$|NASICON|(Na—Ti—O) Electrochemical Cell*; Solid State Ionics, 157, (2003); pp. 357 to 363). A sensing electrode reaction as shown below has been proposed.

$$2Li^+ (\text{or } Ba^{2+}) + CO_2 + 1/2O_2 + 2e^- = Li_2(\text{or Ba})CO_3 \quad (1)$$

The reference electrode reaction is written as shown below.

$$2Li^+ + 1/2O_2 + 2e^- = Li_2O \quad (2)$$

When the activities of $Li_2CO_3$ are constant, the EMF values can be expressed as shown in Equation (3) below.

$$E = E_0 - RT/2F \ln P(CO_2) \quad (3)$$

Where, the parameter 2 in Equation (3) denotes the number of electrons taking part in the sensing electrode reaction. FIG. 4 shows the experimental dependency of E versus log $P(CO_2)$. For the sensor with pure $Li_2CO_3$, the slopes of the Nerstian equation are different between dry and humid conditions. This may result from the deterioration of $Li_2CO_3$ into other compounds such as LiOH, $LiHCO_3$ and $Li_2CO_3 \cdot xH_2O$ in the presence of water vapor, though the specific reason is unknown. The sensor with $BaCO_3$ coated on $Li_2CO_3$ electrode is shown to give same Nerstian slopes of dry and humid conditions, which are very close to the theoretical value for the number of electrons (n=2) for sensing electrode reaction. However, the constant $E_0$ of Equation (3) has values different from those observed for the $Li_2CO_3$ electrode. This reflects that the activity of $Li_2CO_3$ in Equation (1) changes when the $Li_2CO_3$ electrode is coated with $BaCO_3$.

The Role of BaCO$_3$ Coating:

In one embodiment, it is believed that the BaCO$_3$ coating on Li$_2$CO$_3$ electrode contributes to the increase in resistance against humidity as a chemical and physical barrier. The outer BaCO$_3$ layer plays a role as a physical barrier of hindering diffusion of water vapor, while the inner Li$_2$CO$_3$ layer does the CO$_2$ sensing. The BaCO$_3$ layer did not affect on the activity of Li ion because the sensor with BaCO$_3$ coated on Li$_2$CO$_3$ showed the same sensitivity with the sensor with pure Li$_2$CO$_3$ under dry conditions. The difference in affinity of water between BaCO$_3$ and Li$_2$CO$_3$ provides the effect of chemical barrier. The solubility of Li$_2$CO$_3$ in water is 0.0065 grams at 100° C., and that of BaCO$_3$ in water is negligible. Such low affinity of BaCO$_3$ to water may contribute high resistance against humidity. Other binary systems such as Li$_2$CO$_3$—CaCO$_3$ and Na2CO$_3$—SrCO3 are also found to show similar stability in the presence of water vapor because CaCO$_3$ and SrCO$_3$ have no solubility in water (see, e.g., N. Miura, S. Yao, Y. Shimizu, N. Yamazoe; *High Performance Solid Electrolyte Carbon Dioxide Sensor With a Binary Carbonate Electrode*; Sensors and Actuators B, 9 (1992); pp. 165 to 170; and Yao, S. Hosohara, Y. Shimizu, N. Miura, H. Futata, N. Yamazoe; *Solid Electrolyte CO$_2$ Sensor Using NASICON and Li-Based Binary Carbonate Electrode*; Chemistry Letters, 31 (1991); pp. 2069 to 2072).

A potentiometric CO$_2$ gas sensor with lithium phosphate electrolyte is fabricated with a sensing electrode of BaCO$_3$ coated on Li$_2$CO$_3$ and it shows excellent performance toward CO$_2$ monitoring at 500° C. under dry tests as well as under humid tests. In addition, the sensor showed good reproducibility and long-term stability under humid conditions. All sensors showed the Nerstian behavior in good agreement with the theoretical response. To form the BaCO$_3$ layer on Li$_2$CO$_3$, a wet chemical process is used. The coating layer of BaCO$_3$ is an effective approach to improve the sensor stability against humidity. In the layered structure of sensing electrode, the outer BaCO$_3$ layer improves the resistance against humidity as chemical and physical barriers, while the inner Li$_2$CO$_3$ layer is responsible for the CO$_2$ sensing.

Although the invention has been shown and described with respect to certain embodiments, it is obvious that equivalent alterations and modifications will occur to others skilled in the art upon the reading and understanding of this specification. In particular with regard to the various functions performed by the above described components, the terms (including any reference to a "means") used to describe such components are intended to correspond, unless otherwise indicated, to any component which performs the specified function of the described component (e.g., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A carbon dioxide sensor comprising:
    an alkaline metal phosphate substrate;
    at least two conductive leads;
    at least one reference electrode; and
    at least one sensing electrode,
    wherein the sensing electrode is formed from an alkaline carbonate located on the alkaline metal phosphate substrate, and wherein the alkaline carbonate sensing electrode is top-coated with an alkaline earth carbonate.

2. The carbon dioxide sensing electrode of claim 1, wherein the substrate is formed from lithium phosphate and the at least one sensing electrode is formed from lithium carbonate coated with barium carbonate.

3. The carbon dioxide sensing electrode of claim 2, wherein the alkaline metal phosphate substrate is positioned between the at least one sensing electrode formed from lithium carbonate and the at least one reference electrode formed from a combination of an alkaline titanate and titanium (IV) oxide.

4. The carbon dioxide sensing electrode of claim 1, wherein the substrate is formed from sodium phosphate and the at least one sensing electrode is formed from sodium carbonate coated with barium carbonate.

5. The carbon dioxide sensor of claim 1, wherein the sensor exhibits sensitivity up to a temperature of at least about 700° C.

6. The carbon dioxide sensor of claim 1, wherein the sensor exhibits sensitivity up to a temperature of at least about 500° C.

7. The carbon dioxide sensor of claim 1, wherein the sensor exhibits sensitivity up to a temperature of at least about 400° C.

8. The carbon dioxide sensor of claim 1, wherein the sensor exhibits sensitivity at a relative humidity of at least about 50 percent.

9. The carbon dioxide sensor of claim 1, wherein the sensor exhibits sensitivity at a relative humidity of at least about 95 percent.

10. The carbon dioxide sensor of claim 1, wherein the conductive leads are formed from at least one conductive metal selected from gold, silver, copper, or combinations of two or more thereof.

11. The carbon dioxide sensor of claim 1, wherein the at least one reference electrode is formed from a combination of an alkaline titanate and titanium (IV) oxide.

12. The carbon dioxide sensing electrode of claim 1, wherein the alkaline earth carbonate coating forms a barrier layer that completely covers the exposed surface of the alkaline carbonate layer.

13. The carbon dioxide sensing electrode of claim 1, wherein the alkaline metal phosphate substrate is positioned between the at least one reference electrode and the least one sensing electrode.

14. The carbon dioxide sensor of claim 1, wherein the conductive leads are formed from at least one conductive metal selected from gold, silver, copper, or combinations of two or more thereof.

15. The carbon dioxide sensor of claim 1, wherein the at least one reference electrode is formed from a combination of an alkaline titanate and titanium (IV) oxide.

16. A carbon dioxide sensor comprising:
    a lithium phosphate substrate;
    at least two conductive leads;
    at least one reference electrode; and
    at least one sensing electrode,
    wherein the sensing electrode is formed from lithium carbonate located on the alkaline metal phosphate substrate, wherein the lithium carbonate sensing electrode is top-coated with barium carbonate, and wherein the sensor exhibits sensitivity up to a temperature of at least about 700° C.

17. The carbon dioxide sensor of claim 16, wherein the sensor exhibits sensitivity up to a temperature of at least about 500° C.

18. The carbon dioxide sensor of claim 16, wherein the sensor exhibits sensitivity up to a temperature of at least about 400° C.

19. The carbon dioxide sensor of claim 16, wherein the sensor exhibits sensitivity at a relative humidity of at least about 50 percent.

20. The carbon dioxide sensor of claim 16, wherein the sensor exhibits sensitivity at a relative humidity of at least about 80 percent.

21. The carbon dioxide sensor of claim 16, wherein the sensor exhibits sensitivity at a relative humidity of at least about 95 percent.

22. The carbon dioxide sensor of claim 16, wherein the conductive leads are formed from at least one conductive metal selected from gold, silver, copper, or combinations of two or more thereof.

23. The carbon dioxide sensor of claim 16, wherein the at least one reference electrode is formed from a combination of an alkaline titanate and titanium (IV) oxide.

24. The carbon dioxide sensing electrode of claim 16, wherein the barium carbonate coating forms a barrier layer that completely covers the exposed surface of the lithium carbonate layer.

25. The carbon dioxide sensing electrode of claim 16, wherein the lithium phosphate substrate is positioned between the at least one reference electrode and the at least one sensing electrode.

26. The carbon dioxide sensing electrode of claim 16, wherein the lithium phosphate substrate is positioned between the at least one sensing electrode formed from lithium carbonate and the at least one reference electrode formed from a combination of an alkaline titanate and titanium (IV) oxide.

27. A carbon dioxide sensor comprising:
a lithium phosphate substrate;
at least two conductive gold leads;
at least one reference electrode formed from a combination of lithium titanate and titanium (IV) oxide; and
at least one sensing electrode formed from lithium carbonate located on the alkaline metal phosphate substrate, wherein the lithium carbonate sensing electrode is top-coated with barium carbonate,
wherein the sensor exhibits sensitivity up to a temperature of at least about 700° C. regardless of the level of relative humidity present.

28. The carbon dioxide sensor of claim 27, wherein the sensor exhibits sensitivity at a relative humidity of at least about 50 percent.

29. The carbon dioxide sensing electrode of claim 27, wherein the barium carbonate coating forms a barrier layer that completely covers the exposed surface of the lithium carbonate layer.

30. The carbon dioxide sensing electrode of claim 27, wherein the lithium phosphate substrate is positioned between the at least one reference electrode and the least one sensing electrode.

31. The carbon dioxide sensing electrode of claim 27, wherein the lithium phosphate substrate is positioned between the at least one sensing electrode formed from lithium carbonate and the at least one reference electrode formed from a combination of an lithium titanate and titanium (IV) oxide.

32. A carbon dioxide sensor comprising:
an alkaline metal phosphate substrate;
at least two conductive leads;
at least one reference electrode; and
at least one sensing electrode,
wherein the sensing electrode is formed from an alkaline carbonate coated with an alkaline earth carbonate and wherein the alkaline carbonate forms a layer that is located between the alkaline metal phosphate substrate and a layer formed from the alkaline earth carbonate.

33. The carbon dioxide sensing electrode of claim 32, wherein the substrate is formed from lithium phosphate and the at least one sensing electrode is formed from a layer of lithium carbonate coated with a layer of barium carbonate.

34. The carbon dioxide sensing electrode of claim 32, wherein the substrate is formed from sodium phosphate and the at least one sensing electrode is formed from a layer of sodium carbonate coated with a layer of barium carbonate.

35. The carbon dioxide sensor of claim 32, wherein the sensor exhibits sensitivity up to a temperature of at least about 700° C.

36. The carbon dioxide sensor of claim 32, wherein the sensor exhibits sensitivity up to a temperature of at least about 500° C.

37. The carbon dioxide sensor of claim 32, wherein the sensor exhibits sensitivity up to a temperature of at least about 400° C.

38. The carbon dioxide sensor of claim 32, wherein the sensor exhibits sensitivity at a relative humidity of at least about 50 percent.

39. The carbon dioxide sensor of claim 32, wherein the sensor exhibits sensitivity at a relative humidity of at least about 95 percent.

* * * * *